United States Patent [19]

Tomoda et al.

[11] Patent Number: 4,885,759

[45] Date of Patent: Dec. 5, 1989

[54] MEASUREMENT APPARATUS EMPLOYING RADIATION

[75] Inventors: Toshimasa Tomoda; Shinji Badono; Masaki Komaru, all of Amagasaki, Japan

[73] Assignees: Mitsubishi Denki Kabushiki Kaisha, Japan; Petro-Canada, Inc., Canada

[21] Appl. No.: 124,558

[22] Filed: Nov. 24, 1987

[30] Foreign Application Priority Data

Nov. 25, 1986 [JP] Japan .................................. 61-280553

[51] Int. Cl.$^4$ ............................................ G01N 23/06
[52] U.S. Cl. .................................. 378/53; 378/51; 250/363.01; 356/436
[58] Field of Search ........................ 378/44, 45, 47, 51, 378/53, 54, 145, 146, 149, 148, 157; 250/356.1, 358.1, 363.9, 363.06, 363.10, 390.10

[56] References Cited

U.S. PATENT DOCUMENTS

| | | | |
|---|---|---|---|
| 2,591,536 | 4/1952 | Gieringer et al. | 378/148 |
| 3,100,261 | 8/1963 | Bigelow | 378/53 |
| 3,746,874 | 7/1973 | Ohata et al. | 250/358 |
| 3,894,234 | 7/1975 | Mauch et al. | 378/146 |
| 4,075,483 | 2/1978 | Tancrell et al. | 250/363.06 |
| 4,090,074 | 5/1978 | Watt et al. | 378/53 |
| 4,228,353 | 10/1980 | Johnson | 250/356 |
| 4,506,374 | 3/1985 | Flynn | 378/149 |
| 4,562,584 | 12/1985 | Narabayashi | 378/146 |
| 4,638,499 | 1/1987 | Eberhard et al. | 378/149 |
| 4,644,578 | 2/1987 | Paolini | 378/146 |

OTHER PUBLICATIONS

Abstract of Japanese Laid—Open Publication No. 58-151517.
Automatic Petroleum Analytic Apparatus, ND5801 (publication date unknown) Products Catalogue by Mitsubishi Denki Kabushiki Kaisha.
Calorimeter for Heauyoil, ND-5360 ND 5363 (publication date unknown) Products Catalogue by Mitsubishi Denki Kabushiki Kaisha.
Recent Developments of Two—Phase Flow Instrumentation Related with Light Water Reactor Safety Research, Japan At Energy Res. Inst. vol. 23, No. 1, (1981), pp. 28-36.

Primary Examiner—Janice A. Howell
Assistant Examiner—John C. Freeman
Attorney, Agent, or Firm—Leydig, Voit & Mayer

[57] ABSTRACT

A measuring apparatus for measuring a physical property of a substance using radiation has a source of radiation for irradiating the substance, a radiation detector which is disposed on the opposite side of the substance from the radiation source, a mask for allowing radiaton to enter the radiation detector only along n prescribed pathways, and a signal processing and calculating device for calculating the physical property of the substance based on the radiation which is incident upon the radiation detector. The mask has n different mask patterns each comprising a plurality of pattern elements which allow the passage of radiation and which can be positioned between the substance and the radiation detector in alignment with the radiation pathways.

8 Claims, 2 Drawing Sheets

MEASUREMENT APPARATUS EMPLOYING RADIATION

BACKGROUND OF THE INVENTION

This invention relates to an apparatus for measuring the spatial average of a physical property of a substance using radiation, the term "radiation" being here used to refer to all forms of electromagnetic radiation including X-rays, gamma rays, and visible light. More particularly but not exclusively, it relates to a component analyzer for determining the proportions of the components in a multi-component fluid flowing through a pipe.

FIG. 1 is a schematic diagram of a conventional measuring apparatus in the form of a component analyzer which employs radiation to analyze the components of a fluid within a pipe. In the figure, element number 1 is a radiation source which produces X-rays or gamma rays, element number 2 is the radiation which is emitted from the radiation source 1, element number 3 is a pipe which is irradiated with this radiation 2, element number 4 is a two-component fluid to be measured which is flowing through the pipe 3, element number 5 is a collimator which is disposed on the opposite side of the pipe 3 from the radiation source 1, element number 6 is a through hole which is formed in the collimator 5 and through which radiation can pass, element number 7 is a radiation detector which detects the radiation 2 which passes through the through hole 6, and element number 8 is a signal processing and calculating device which processes the signal from the radiation detector 7 and outputs a signal corresponding to some physical property of the fluid 3 being measured.

The attenuation of radiation such as X-rays or gamma rays passing through a substance is expressed by the following equation.

$$I = I_o \exp(-\mu \rho t) \quad (1)$$

wherein $I_o$ is the intensity of the incident radiation, $\mu$ is the absorption coefficient with respect to radiation of the substance through which the radiation is passing, $\rho$ is the specific gravity of the substance, $t$ is the thickness of the substance through which the radiation passes, and $I$ is the intensity of the radiation after passing through the thickness $t$. When the fluid 4 of FIG. 1 comprises a first substance and a second substance and the specific gravities thereof are respectively $\rho_1$ and $\rho_2$, the mass absorption coefficients with respect to the radiation are respectively $\mu_1$ and $\mu_2$, the thicknesses of the first and second substances through which the radiation passes are respectively $t_1$ and $t_2$, and the length of the path along which the radiation passes where the thicknesses are measured is $L$, then the following relationships hold.

$$\mu_1 \rho_1 t_1 + \mu_2 \rho_2 t_2 = \ln(I_o/I) - a \quad (2)$$

$$t_1 + t_2 = L \quad (3)$$

$a$ is a constant which is determined by the material, the thickness, and other characteristics of the pipe 3. The other values $\mu_1, \mu_2, \rho_1, \rho_2, I_o$, and $L$ are known in advance. Therefore, when the proportion of the two components is not known, if the intensity $I$ of radiation after passing through the fluid is measured, the values of $t_1$ and $t_2$ can be found from Equations (2) and (3), and the proportion of the components along the pathway of the radiation can be determined.

In FIG. 1, radiation 2 is emitted from the radiation source 1, it passes through the walls of the pipe 3, the fluid 4 being measured, and the through hole 6 of the collimator 5 and enters the radiation detector 7. Signals from the radiation detector 7 are sent to the signal processing and calculating device 8. Here, $t_1$ and $t_2$ are determined based on Equations (2) and (3), and component analysis along the path of the radiation 2 is performed. The distribution of the two components in the pipe 3 is not necessarily uniform. Therefore, the collimator 5 is successively moved by an unillustrated drive apparatus to a number of different positions to change the location of the through hole 6, and measurement is performed in the same manner at each location. By taking measurements at n different locations, i.e., by measuring the component proportions along n different paths of radiation, and by taking the average of the measurements, an average value of the proportions of the components in a cross section of the fluid 4 is obtained. This average is calculated by the signal processing and calculating device 8.

Equation (2) can also be written as follows.

$$\mu_1 \rho_1 t_1 + \mu_2 \rho_2 t_2 = -\ln(I) + C \quad (4)$$

If each of the n radiation pathways is distinguished by a subscript $i$ and summations are performed for the n pathways, then the following equations, which correspond to Equations (2) and (3), can be written.

$$\mu_1 \rho_1 \sum_{i=1}^{n} t_{1i} + \mu_2 \rho_2 \sum_{i=1}^{n} t_{2i} = -\sum_{i=1}^{n} \ln(I_i) + \sum_{i=1}^{n} C_i \quad (5)$$

$$\sum_{i=1}^{n} t_{1i} + \sum_{i=1}^{n} t_{2i} = \sum_{i=1}^{n} L_i \quad (6)$$

The average value of the proportions of components 1 and 2 for all the pathways can be found by determining the value of $$\sum_{i=1}^{n} t_{1i}$$

and $$\sum_{i=1}^{n} t_{2i},$$

so it is only necessary to determine $$\sum_{i=1}^{n} \ln(I_i),$$

and it is not required to find the individual values of $\ln(I_i)$ or $I_i$. Namely, the average value of the component proportions over a cross section can be found by determining the sum of the logarithms of a quantity related to the radiation 2, i.e., the intensity $I$ of the radiation after passing along each of the n pathways.

The radiation 2 is a type of quantum, and therefore the output signal from the radiation detector 7 signal exhibits a constant statistical fluctuation. The measurement error due to this fluctuation decreases in inverse proportion to the square root of the measurement time if the intensity of the radiation 2 is constant. Therefore, in order to perform highly accurate measurement, a long measurement time is necessary. Furthermore, if the through hole 6 of the collimator 5 is successively moved to n different location and n separate measurements of radiation are made, the time required for measurement becomes roughly n times that required for measurement of a single pathway. Therefore, highly accurate measurement requires a very long time.

SUMMARY OF THE INVENTION

It is therefore the object of the present invention to provide a measuring apparatus which can determine the spatial average of a physical property of an object being measured with high accuracy in a short period of time.

A measuring apparatus in accordance with the present invention comprises a source of radiation which is disposed on one side of a substance being measured, a radiation detector which is disposed on the other side of the substance, a mask for enabling radiation to enter the radiation detector only along n different pathways, where n is an integer greater than 1, and a signal processing and calculating device which processes the signals from the radiation detector and produces an output signal corresponding to the value of a physical property of the substance. The mask has n different mask patterns formed thereon, each mask pattern comprising a plurality of pattern elements which are capable of allowing the passage of radiation through the mask to the radiation detector along one of the n pathways. Each of the mask patterns can be moved into a position between the substance and the radiation detector such that each of its pattern elements is aligned with one of the n radiation pathways.

The measuring apparatus of the present invention can be used to measure various physical properties of a substance using radiation, but in a preferred embodiment, the measuring apparatus is a component analyzer which measures the proportions of the components of a fluid flowing through a pipe by measuring the attenuation of radiation passing through the fluid.

The mask is not restricted to any particular shape, but in a preferred embodiment, the mask is in the form of a rotating cylinder which surrounds the radiation detector, and each of the mask patterns comprises a plurality of through holes which are formed in the wall of the cylinder. The mask patterns are spaced around the circumference of the cylinder. By rotating the cylinder about its longitudinal axis, each of the mask patterns can be brought one at a time into a position between the radiation detector and the substance being measured so that each of the through holes is aligned with one of the radiation paths.

The present invention may further comprise a collimator for collimating the radiation which enters the radiation detector. In a preferred embodiment, a stationary collimator is employed which has n through holes formed therein corresponding to the n pathways of radiation. Radiation can enter the radiation detector only when the through holes of the mask patterns are aligned with the through holes of the collimator. The through holes of the collimator preferably have a smaller diameter than the through hole of the mask patterns.

BRIEF DESCRIPTION OF THE DRAWINGS

In the figures, the same reference numerals indicate the same or corresponding parts.

DESCRIPTION OF THE PREFERRED EMBODIMENTS

Figure 1:
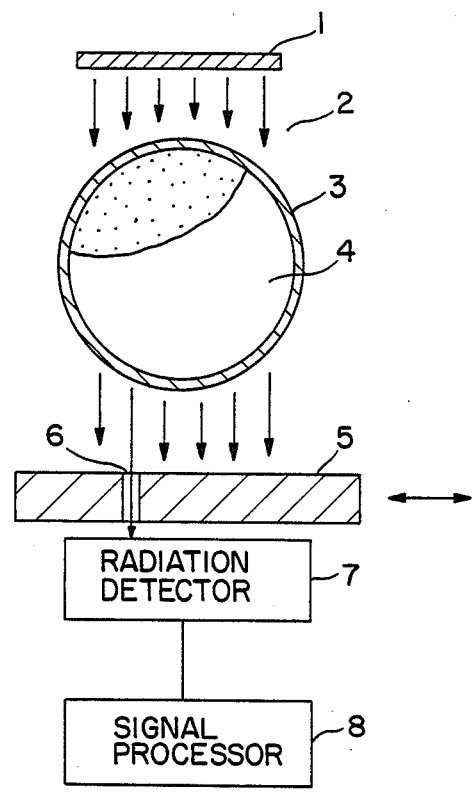
FIG. 1 is a schematic cross-sectional view of a conventional component analyzer.

An embodiment of a component analyzer in accordance with the present invention will now be described while referring to FIG. 2 of the accompanying drawings, which is a schematic cross-sectional view of this embodiment. Elements numbers 1–4, 7 and 8 are identical to the corresponding elements in FIG. 1 and an explanation thereof will be omitted. Element number 5a is a stationary collimator which has n through holes 6a formed therein at roughly equal intervals, wherein n is an odd or even number. Element number 9 is an encoded mask in the form of a rotating cylinder having n different mask patterns formed around its circumference. Each of the mask patterns comprises a plurality of pattern elements in the form of through holes 10, each of which can be aligned with one of the through holes 6A in the collimator 5A. Element number 11 is a drive motor for rotating the encoded mask 9 about its longitudinal axis.

The stationary collimator 5A is secured between the radiation detector 7 and the rotating mask 9. The through holes 6A of the stationary collimator 5A have a smaller diameter than the through holes 10 of the rotating encoded mask 9. The encoded mask 9 can be rotated by the drive motor 11 among n different rotational positions corresponding to the n different mask patterns. When the mask 9 is stopped in any one of the n positions, the through holes 10 of the corresponding mask pattern are aligned with the through holes 6a in the collimator 5A. The through holes 6A are opened in the stationary collimator 5A so that the radiation which passes through these through holes 6A passes the cross section of the pipe 3 with a nearly uniform density.

Figure 2:
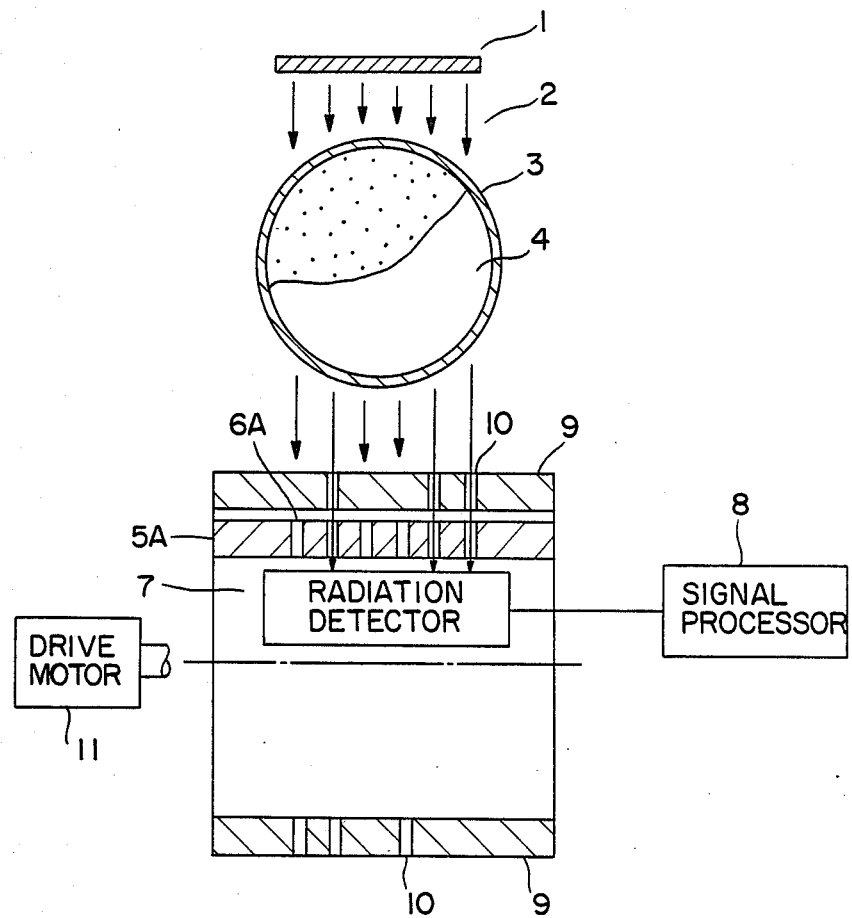
FIG. 2 is a schematic cross-sectional view of an embodiment of a component analyzer in accordance with the present invention.

In the same manner as with the conventional apparatus of FIG. 1, the intensity of the radiation which passes through the fluid 4 is measured by the radiation detector 7, and component analysis is performed based on the measured value. However, the present invention differs from the conventional apparatus in that at rotational position of the encoded mask 9, the radiation intensity is simultaneously measured for a plurality of the n pathways of radiation through the fluid 4. The drive motor 11 rotates the rotating mask 9 and stops it at each of n different positions in which the through holes 10 of one of the mask patterns are aligned with the through holes 6A of the collimator 5A. For each mask pattern, the radiation detector 7 measures the total amount of radiation passing through the through holes 10 of that pattern. A complete set of data consists of one measurement for each mask pattern, or a total of n measurements. Based on this data, the signal processing and calculating device 8 calculates the radiation intensity for each point, calculates the sum of the logarithms thereof, calculates $$\sum_{i=1}^{n} t_{1i}, \sum_{i=1}^{n} t_{zi}$$

in accordance with Equations (5) and (6), and determines the cross-sectional average for the proportions of the two components. As will become clear from the subsequent explanation, the measurement error due to statistical error is small compared to the case in which measurements are made one time at each of n locations.

When the rotating encoded mask 9 is rotated between positions, it is difficult to stop the mask 9 at precisely the same position each time with respect to the collimator 5A. For this reason, the diameter of the through holes 6A of the stationary collimator 5A is smaller than the diameter of the through holes 10 of the rotating encoded mask 9. Therefore, even if there is some deviation in the rotational position of the rotating encoded mask 9 and the through holes 6A and 10 are not exactly aligned, the amount of radiation which is incident upon the radiation detector 7 will not vary, and no measurement error is produced.

Next, the theory behind a measuring apparatus of the present invention will be explained.

It will be assumed that a mask comprises n different mask patterns corresponding to n different measurement points in space. Each mask pattern comprises a plurality of pattern elements. Each pattern element is in the form of a through hole which allows the passage of quantums of radiation into a radiation detector, or else is a shielding element which prevents the passage of radiation. The mask patterns are placed one at a time in front of a radiation detector, and measurement is carried out for a period of time $\Delta t$ for each mask pattern. Measurement is performed one time for each mask pattern, or a total of n times, to obtain a complete set of data. Accordingly, the total measurement time is $n\Delta t$. The value obtained for a single measurement for a given mask pattern is the sum of the intensities of the radiation passing along the paths corresponding to the through holes in that mask pattern. If the n mask patterns are independent of one another, then the unknown values for the n pathways can be determined by a total of n measurements.

It will be assumed that $\hat{x}$ is a vector of the intensity of the radiation at each of the n points, $\hat{d}$ is a vector comprising n measured values for a mask pattern, and M is a matrix of the positions of the through holes of the n mask patterns. Each element of M is either 1 or 0. A value of 1 corresponds to a through hole which passes radiation, and a 0 corresponds to a shielding element which blocks radiation. The relationship between $\hat{d}$, M, and $\hat{x}$ is $$\hat{d} = M \cdot \hat{x} \tag{7}$$

If M has an inverse matrix $M^{-1}$, i.e., if the n mask patterns are independent of one another, then $$\hat{x} = M^{-1} \cdot M \hat{x} = M^{-1} \cdot \hat{d} \tag{8}$$

and the value of $\hat{x}$ for each point can be determined from the measured value $\hat{d}$.

The method employed with a conventional apparatus in which measurement is performed for one point at a time is a special case in which M is the identity matrix.

If M is created based on a Hadamard matrix, then $M^{-1}$ is a matrix with elements equal to $\pm 1$, and element $x_i$ of $\hat{x}$ is found by addition and subtraction of the elements of $\hat{d}$. For example, if n=7, then $$M = \begin{pmatrix} 1 & 0 & 0 & 1 & 0 & 1 & 1 \\ 0 & 0 & 1 & 0 & 1 & 1 & 1 \\ 0 & 1 & 0 & 1 & 1 & 1 & 0 \\ 1 & 0 & 1 & 1 & 1 & 0 & 0 \\ 0 & 1 & 1 & 1 & 0 & 0 & 1 \\ 1 & 1 & 1 & 0 & 0 & 1 & 0 \\ 1 & 1 & 0 & 0 & 1 & 0 & 1 \end{pmatrix} \tag{9}$$

$$M^{-1} = \begin{pmatrix} + & - & - & + & - & + & + \\ - & - & + & - & + & + & + \\ - & + & - & + & + & + & - \\ + & - & + & + & + & - & - \\ - & + & + & + & - & - & + \\ + & + & + & - & - & + & - \\ + & + & - & - & + & - & + \end{pmatrix} \tag{10}$$

wherein + stands for +1 and − stands for −1.

In this case, $$MM^{-1} + = \begin{pmatrix} 4 & 0 & 0 & 0 & 0 & 0 & 0 \\ 0 & 4 & 0 & 0 & 0 & 0 & 0 \\ 0 & 0 & 4 & 0 & 0 & 0 & 0 \\ 0 & 0 & 0 & 4 & 0 & 0 & 0 \\ 0 & 0 & 0 & 0 & 4 & 0 & 0 \\ 0 & 0 & 0 & 0 & 0 & 4 & 0 \\ 0 & 0 & 0 & 0 & 0 & 0 & 4 \end{pmatrix} \tag{11}$$

Accordingly, $4\hat{x} = M^{-1} \cdot \hat{d}$, and it can be seen that x is found by the addition or subtraction of $d_j$. Each row and column of M has four 1's and three 0's, and each row and column of $M^{-1}$ has four +1's and three −1's. If element $(M^{-1})_{ij}$ of $M^{-1}$ is expressed as follows, $$(M^{-1})_{ij} = S_{ij} \tag{12}$$

then the following relationship holds $$\Sigma_i S_{ij} = \Sigma_j S_{ij} = 1 \tag{13}$$

In the above-described case in which n=7, there are 4 through holes, and $4x_i$ was found by the addition and subtraction of $d_j$. In general, however, when forming a matrix M based on a Hadamard matrix, each row and column has $(n+1)/2$ through holes, and $[(N+1)/2]/x_i$ is found by n additions and subtractions. Namely, it is equal to $$x_i = \frac{2}{n+1} \sum_j S_{ij} d_j \tag{14}$$

Next, it will be shown that the statistical error $\Sigma_i$ ln $(x_i)$ using an encoded mask of the present invention is smaller than for a conventional apparatus in which $x_i$ is measured only once. First, as a simple case, it will be assumed that the intensity of radiation is nearly uniform for each of the n points at which measurement is performed, and the measured value is N counts per second at each point. In the conventional method in which $x_i$ is measured once, the measurement time for one point is $\Delta t$, and the total measurement time is $n\Delta t$, just as when using an encoded mask. The expection $\bar{x}_i$ of $x_i$ is $$\bar{x}_i = N\Delta t \quad (15)$$

The statistical error $\sigma_{xi}$ of $x_i$ is $$\sigma_{xi} = \sqrt{N\Delta t} \quad (16)$$

The relative statistical error $\sigma_{xi}/\bar{x}_i$ is $$\sigma_{xi}/\bar{x}_i = \frac{1}{\sqrt{N\Delta t}} \quad (17)$$

When using an encoded mask, from Equations (13) and (14) and the following equation, $$d_j = \frac{n+1}{2} N\Delta t \quad (18)$$

the following equation is obtained.

$$\bar{x}_i = N\Delta t \quad (19)$$

If the statistical errors of the n values of $x_i$ which are given by Equation (14) are transmitted with equal weight to the statistical error of $d_j$, then the statistical error $\sigma_{dj}$ of $d_j$ is given by $$\sigma_{dj} = \sqrt{\frac{n+1}{2} N\Delta t} \quad (20)$$

Therefore, $$\sigma_{\Sigma xi} = \frac{2}{n+1} \sqrt{n} \sqrt{\frac{n+1}{2} N\Delta t} \quad (21)$$
$$= \sqrt{\frac{2}{n+1}} \sqrt{nN\Delta t}$$

Next, the statistical error of $\Sigma \ln(x_i)$ will be evaluated. In general, when $\Delta x/\bar{x}_i$ is small, $$\ln(x_i + \Delta x_i) = \ln(x_i) + \frac{\Delta x_i}{x_i} \quad (22)$$

In the conventional method, from Equations (15) and (17), $$\sum_i \ln(x_i) = x_i \ln(N\Delta t) \quad (23)$$

$$\sigma_{\sum_i \ln(x_i)} = \frac{\sqrt{n}}{\sqrt{N\Delta t}} \quad (24)$$

Accordingly, the signal-to-noise ratio with respect to the statistical error of $\Sigma_i \ln(x_i)$ is $$SNR = \frac{n \ln(N\Delta t)}{\sqrt{n} \sqrt{N\Delta t}} \quad (25)$$
$$= \sqrt{\frac{n}{N\Delta t}} \ln(N\Delta t)$$

On the other hand, when using the encoded mask of the present invention, from Equation (14), $$\Delta x_i = \frac{2}{n+1} \Sigma S_{ij} \Delta d_j$$
$$\sum_i x_i = \frac{2}{n+1} \Sigma \Sigma S_{ij} d_j$$
$$= \frac{2}{n+1} \Sigma_j \left( \Sigma_i S_{ij} \right) d_j$$

and from Equation (13)

$$\sum_i x_i = \frac{2}{n+1} \Sigma d_y \quad (26)$$

Accordingly, $$\Sigma_i \Delta x_i = \frac{2}{n+1} \Sigma_i \Sigma_j S_{ij} \Delta S_j$$
$$= \frac{2}{n+1} \Sigma_j \left( \Sigma_i S_{ij} \right) \Delta d_j$$
$$= \frac{2}{n+1} \Sigma \Delta d_j$$

and from Equation (26), $$\Sigma_i \Delta x_i = \Delta(\Sigma_i x_i) \quad (27)$$

The expectation of $\Sigma \ln(x_i)$ is the same as for the conventional method, and is given by the following equation.

$$\Sigma_i \ln(\bar{x}_i) = n \ln(N\Delta t) \quad (28)$$

From Equation (22), (19), (27), and (21), the statistical error $\sigma \Sigma_i \ln(x_i)$ is found to be $$\sigma_{\sum_i \ln(x_i)} = \frac{\sigma_{\Sigma xi}}{N\Delta t} \quad (29)$$
$$= \frac{\sqrt{\frac{2}{N+1}} \sqrt{nN\Delta t}}{N\Delta t}$$
$$= \sqrt{\frac{2}{n+1}} \sqrt{\frac{n}{N\Delta t}}$$

By combining Equations (28) and (29), the signal-to-noise ratio is found to be $$SNR = \sqrt{nN\Delta t} \ln(N\Delta t) \sqrt{\frac{n+1}{2}} \quad (30)$$

By comparing Equations (25) and (30), it can be seen that the signal-to-noise ratio when using an encoded mask is $$\sqrt{\frac{n+1}{2}}$$

times better than that when using the conventional method.

In the above explanation, it was assumed that the intensity of radiation is nearly the same at each of n points in space. However, the same result is obtained when the intensity differs at the n points. This was confirmed by a computer simulation in which random numbers with a normal distribution were generated. Simulation was performed 100 times, and the signal-to-noise ratio was compared for the conventional method and a method using an encoded mask with a plurality of mask patterns. There was some dispersion, but when n=7, the signal-to-noise ratio when using an encoded mask was 1.5–2 times better than for the conventional method. When $$n = 7, \sqrt{\frac{n+1}{2}} = 2.$$

Therefore, the simulation showed good agreement with the analysis for the case in which the intensity is nearly uniform for each of the n points.

In the manner described above, in accordance with this invention, in order to determine the average value of a physical property of a fluid which is dispersed in a space, the intensity of quantums of radiation is measured at n points, and in order to determine the sum of the logarithms of the values, a plurality of mask patterns having a plurality of through holes are employed. Therefore, the statistical error of the sum of n logarithms of the intensity of the radiation becomes small, and the accuracy of the average value of the physical property being measured is increased.

In the above-described embodiment, a rotating encoded mask 9 and a stationary collimator 5A are employed. However, it is possible to employ a collimator as a mask by forming n different mask patterns consisting of through holes in the collimator and moving the collimator. Furthermore, the encoded mask or collimator need not be rotated but may be moved linearly so as to bring each of the mask patterns in front of the radiation detector. Furthermore, instead of employing a mask comprising a cylinder having n different mask patterns, it is possible to employ a mask comprising n interchangeable mask plates each having a different mask pattern formed thereon. Furthermore, the longitudinal axis of the rotating encoded mask is illustrated as being on the lower side of the radiation detector 7, but it can be disposed between the radiation detector 7 and the pipe 3.

When mask patterns are formed on the surface of a rotating encoded mask 9, the through holes or shielding elements which constitute the pattern elements need not be arranged in a straight line. They may be arranged in two lines, or they may be staggered in order to save space.

In the above-described embodiment, the stationary collimator 5A is disposed on the inside of the rotating encoded mask 9, but it can instead be disposed on the outside.

Furthermore, the above-described embodiment was explained for the case in which the fluid 4 consists of two components, but the present invention may also be employed to analyze a fluid having three components. Analysis of three components can be performed by employing two types of energy having different photon energies.

In addition to being used for component analysis of a fluid, the present invention can be used to measure densities or the amount of impurities. In fact, the present invention can be employed as any type of apparatus which in order to determine the spatial average of a physical property of a substance which is distributed in a space measures the intensity of quantums of radiation at n points and finds the sum of the logarithms of the measured intensities.

What is claimed is:

1. A measuring apparatus for determining the spatial average of a physical property of a substance, comprising:
    irradiating means for irradiating said substance with radiation;
    radiation detecting means for measuring the intensity of the radiation which is incident upon said radiation detecting means and producing a corresponding output signal, said radiation detecting means being disposed on the opposite side of said substance from said irradiating means;
    a mask for enabling the radiation from said irradiating means to reach said radiation detecting means only along n different pathways which pass through said substance, wherein n is an integer greater than 1, said mask being disposed between said radiation detecting means and said substance, said mask having n different mask patterns, each of said mask patterns comprising a plurality of pattern elements which transmit the radiation;
    drive means for individually moving each of said mask patterns into a position such that each of the pattern elements is aligned with one of said pathways; and
    processing means for processing said corresponding output signal from said radiation detecting means and producing a second output signal corresponding to said physical property of said substance.

2. A measuring apparatus as claimed in claim 1 wherein:
    said mask is a cylinder which surrounds said radiation detecting means and has n different mask patterns formed around the circumference thereof; and
    said drive means comprises means for rotating said cylinder about a longitudinal axis of said cylinder to n different rotational positions.

3. A measuring apparatus as claimed in claim 2 wherein said pattern elements comprise through holes which are formed in said cylinder.

4. A measuring apparatus as claimed in claim 1 wherein said mask comprises a cylinder having n different mask patterns formed thereon.

5. A measuring apparatus as claimed in claim 1 further comprising collimating means for collimating said radiation passing along said n pathways before said radiation enters said radiation detecting means.

6. A measuring apparatus as claimed in claim 5 wherein said collimating means comprises a stationary collimator having n through holes formed therein, each of which is aligned with one of said n radiation pathways.

7. A measuring apparatus as claimed in claim 6 wherein said pattern elements of said mask are through holes having a larger diameter than the diameter of said through holes of said stationary collimator.

8. A measuring apparatus as claimed in claim 1 wherein said mask comprises a moving collimator having n different mask patterns formed thereon.

* * * * *